US011065221B2

(12) United States Patent
Shytaj et al.

(10) Patent No.: US 11,065,221 B2
(45) Date of Patent: Jul. 20, 2021

(54) BUTHIONINE SULFOXIMINE AND A METALLODRUG FOR THE TREATMENT OF CANCER, HIV OR A RHEUMATIC DISEASE

(71) Applicant: ISTITUTO SUPERIORE DI SANITÀ, Rome (IT)

(72) Inventors: Iart Luca Shytaj, Heidelberg (DE); Shailendra Pratap Singh Rathore, London (GB); Francesco Procopio, Lausanne (CH); Andrea Savarino, Turin (IT)

(73) Assignee: ISTITUTO SUPERIORE DI SANITÀ, Rome (IT)

( * ) Notice: Subject to any disclaimer, the term of this patent is extended or adjusted under 35 U.S.C. 154(b) by 0 days.

(21) Appl. No.: 16/496,039

(22) PCT Filed: Mar. 23, 2018

(86) PCT No.: PCT/EP2018/057557
§ 371 (c)(1),
(2) Date: Sep. 20, 2019

(87) PCT Pub. No.: WO2018/172559
PCT Pub. Date: Sep. 27, 2018

(65) Prior Publication Data
US 2020/0022937 A1   Jan. 23, 2020

Related U.S. Application Data

(60) Provisional application No. 62/475,654, filed on Mar. 23, 2017.

(51) Int. Cl.
| | |
|---|---|
| *A61K 31/10* | (2006.01) |
| *A61K 33/242* | (2019.01) |
| *A61K 31/198* | (2006.01) |
| *A61P 35/00* | (2006.01) |

(52) U.S. Cl.
CPC .......... *A61K 31/198* (2013.01); *A61K 33/242* (2019.01); *A61P 35/00* (2018.01)

(58) Field of Classification Search
None
See application file for complete search history.

(56) References Cited

PUBLICATIONS

Saikawa, Y. et al., "Enhancement of Antitumor Activity of Cisplatin on Human Gastric Cancer Cells in vitro and in vivo by Buthionine Sulfoximine," *Jpn. J. Cancer Res.*, 84: 787-793, 1993.
International Preliminary Report on Patentability, dated Oct. 3, 2019, from International Application No. PCT/EP2018/057557, filed on Mar. 23, 2018.
Anderson, C.P. et al., "Pilot Study of Intravenous Melphalan Combined With Continuous Infusion L-S, R-Buthionine Sulfoximine for Children With Recurrent Neuroblastoma," *Pediatr Blood Cancer*, 62: 1739-1746, 2015.
Bailey, H.H. et al., "Phase I Clinical Trial of Intravenous L-Buthionine Sulfoximine and Melphalan: An Attempt at Modulation of Glutathione," *Journal of Clinical Oncology*, 12(1): 194-205, 1994.
Bailey, H.H. et al., "Phase I Study of Continuous-Infusion L-S,R-Buthionine Sulfoximine With Intravenous Melphalan," *Journal of the National Cancer Institute*, 89(23): 1789-1796, 1997.
Benhar, M. et al., "Dual targeting of the thioredoxin and glutathione systems in cancer and HIV," *Journal of Clinical Investigation*, 126(5); 1630-1639, 2016.
Blanchard, O.L. et al., "Translating dosages from animal models to human clinical trials—revisiting body surface area scaling," *FASEB Journal*, 29: 1629-1634, 2015.
Capparelli, E.V. et al., "Phase I Clinical Trial Results of Auranofin, a Novel Antiparasitic Agent," *Antimicrobial Agents and Chemotherapy*, 61(1): e01947-16; 1-8, 2017.
Fath, M.A. et al., "Enhancement of Carboplatin-Mediated Lung Cancer Cell Killing by Simultaneous Disruption of Glutathione and Thioredoxin Metabolism," *Clinical Cancer Research*, 17(19): 6206-6217, 2011.
Filipczak, P.T. et al., "TSC2 Deficiency Unmasks a Novel Necrosis Pathway That Is Suppressed by the RIP1/RIP3/MLKL Signaling Cascade," *Cancer Research*, 76(24): 7130-7139, 2016.
Griffith, O.W. et al., Potent and Specific Inhibition of Glutathione Synthesis by Buthionine Sulfoximine (S-n-Butyl Homocysteine Sulfoximine), *Journal of Biological Chemistry*, 254(16): 7558-7560, 1979.
Habermann, K.J. et al., "Targeting redox homeostasis in rhabdomyosarcoma cells: GSH-depleting agents enhance auranofin-induced cell death," *Cell Death and Disease*, 8: e3067; 1-14, 2017.
International Search Report and Written Opinion of the International Searching Authority, dated Oct. 17, 2018, from International Application No. PCT/EP2018/057557, filed on Mar. 23, 2018. (20 pages).
Invitation to Pay Additional Fees of the International Searching Authority, dated Jul. 12, 2018, from International Application No. PCT/EP2018/057557, filed on Mar. 23, 2018. (13 pages).
Kachadourian, R. et al., "Selected flavonoids potentiate the toxicity of cisplatin in human lung adenocarcinoma cells: A role for glutathione depletion," *International Journal of Oncology*, 31: 161-168, 2007.
Kiebala, M. et al., "Dual targeting of the thioredoxin and glutathione antioxidan systems in malignant B cells: A novel synergistic therapeutic approach," *Experimental Hematology*, 43(2): 89-99, 2015.
Lopes-Coelho, F. et al., "HNF1β drives glutathione (GSH) synthesis underlying intrinsic carboplatin resistance of ovarian clear cell carcinoma (OCCC)," *Tumor Biology*, 37(4): 4813-4829, 2016.
Malaker, K. et al., "Pharmacodynamics of Prolonged Treatment With L,S-Buthionine Sulfoximine," *Int J. Radiation Oncology Biol. Phys.*, 29(2): 407-412, 1994.

(Continued)

*Primary Examiner* — Samantha L Shterengarts
(74) *Attorney, Agent, or Firm* — HoustonHogle LLP

(57) ABSTRACT

There is disclosed buthionine sulfoximine (BSO) for use in a method of treatment of cancer, HIV or a rheumatic disease. The method comprises administering (a) BSO at a dosage of less than or equal to 50 mg/kg, and (b) a metallodrug at a clinically-acceptable dosage.

15 Claims, 6 Drawing Sheets

(56) References Cited

PUBLICATIONS

Marostica, L.L. et al., "Synergistic Antiproliferative Effects of a New Cucurbitacin B Derivative and Chemotherapy Drugs on Lung Cancer Cell Line A549," *Chemical Research in Toxicology*, 28(10): 1949-1960, 2015.

Mayer, R.D. et al., "Improved use of buthionine sulfoximine to prevent cisplatin nephrotoxicity in rats," *J Cancer Res Clin Oncol*, 115: 418-422, 1989.

Meister, A., "Glutathione Deficiency Produced by Inhibition of Its Synthesis, and Its Reversal; Applications in Research and Therapy," *Pharmac. Ther.*, 51: 155-194, 1991.

Minchinton, A.I. et al., "Glutathione Depletion in Tissues After Administration of Buthionine Sulphoximine," *Int. J Radiation Oncology Biol. Phys.*, 10: 1261-1264, 1984.

O'Dwyer, P.J. et al., "Depletion of Glutathione in Normal and Malignant Human Cells In Vivo by Buthionine Sulfoximine: Clinical and Biochemical Results," *Journal of the National Cancer Institute*, 84(4): 264-267, 1992.

O'Dwyer, P.J. et al., "Phase I Trial of Buthionine Sulfoximine in Combination With Melphalan in Patients With Cancer," *Journal of Clinical Oncology*, 14(1): 249-256, 1996.

Reagan-Shaw, S. et al., "Dose translation from animal to human studies revisited," *FASEB Journal*, 22: 659-661, 2007.

Romero-Canelón, I. et al., "Next-Generation Metal Anticancer Complexes: Multitargeting via Redox Modulation", *Inorganic Chemistry*, 52(21): 12276-12291, 2013.

Rong, L. et al., "Modeling Latently Infected Cell Activation: Viral and Latent Reservoir Persistence, and Viral Blips in HIV-infected Patients on Potent Therapy," *PLOS Computational Biology*, 5(10): e1000533; 1-18, 2009.

Sandor, V. et al., "Quantitation of the diastereoisomers of L-buthionine-(R,S)-sulfoximine in human plasma: a validated assay by capillary electrophoresis," *Journal of Chromatography B*, 673: 123-131, 1995.

Savarino, A. et al., "Chloroquine and beyond: exploring anti-rheumatic drugs to reduce immune hyperactivation in HIV/AIDS," *Retrovirology*, 12(51): 1-10, 2015.

Shytaj, I.L. et al., "Cell-mediated anti-Gag immunity in pharmacologically induced functional cure of simian AIDS: a 'bottleneck effect'?" *Journal of Medical Primatology*, 44(5): 227-240, 2015.

Shytaj, I.L. et al., "Investigational treatment suspension and enhanced cell-mediated immunity at rebound followed by drug-free remission of simian AIDS," *Retrovirology*, 10(71): 1-15, 2013.

Shytaj, I.L. et al., "Two-Year Follow-Up of Macaques Developing Intermittent Control of the Human Immunodeficiency Virus Homolog Simian Immunodeficiency. Virus SIVmac251 in the Chronic Phase of Infection," *Journal of Virology*, 89(15): 7521-7535, 2015.

Starha, P. et al., "Potentiating Effect of UVA Irradiation on Anticancer Activity of Carboplatin Derivatives Involving 7-Azaindoles," *PLOS One*, 10(4): e0123595, 2015. (14 pages).

Suarez-Almazor, M.E. et al., "Auranofin versus placebo in rheumatoid arthritis (Review)," *Cochrane Collaboration, Cochrane Database of Systematic Reviews* 2000, 2(CD002048): 1-35, 2010. (37 pages).

Tsutsui, K. et al., Chemosensitization by Buthionine Sulfoximine In Vivo, *Int. J. Radiation Oncology Biol. Phys.*, 12: 1183-1186, 1986.

Villablanca, J.G. et al., "A Phase I New Approaches to Neuroblastoma Therapy Study of Buthionine Sulfoximine and Melphalan With Autologous Stem Cells for Recurrent/Refractory High-Risk Neuroblastoma," *Pediatr Blood Cancer*, 63: 1349-1356, 2016.

Vint, I.A.M. et al, "The Interaction of Auranofin and Buthionine Sulfoximine Blocks Activation of Human Peripheral T Lymphocytes," *Cellular Immunology*, 152: 152-161, 1993.

Wang, H. et al., "Auranofin radiosensitizes tumor cells through targeting thioredoxin reductase and resulting overproduction of reactive oxygen species," *Oncotarget*, 8 (22): 35728-35742, 2017.

White, Russell D. et al., "The Effect of Buthionine Sulfoximine, an Inhibitor of Glutathione Synthesis, on Hepatic Drug Metabolism in the Male Mouse," *Toxicology Letters*, 23: 25-32, 1984.

You, B.R. et al, "Auranofin induces apoptosis and necrosis in HeLa cells via oxidative stress and glutathione depletion," *Molecular Medicine Reports*, 11: 1428-1434, 2015.

You, B.R. et al., "Auranofin induces mesothelioma cell death through oxidative stress and GSH depletion," *Oncology Reports*, 35(1): 546-551, 2016.

A

B

BUTHIONINE SULFOXIMINE AND A METALLODRUG FOR THE TREATMENT OF CANCER, HIV OR A RHEUMATIC DISEASE

RELATED APPLICATIONS

This application is a § 371 National Phase Application of International Application No. PCT/EP2018/057557, filed on Mar. 23, 2018, now International Publication No. WO 2018/172559, published on Sep. 27, 2018, which International Application claims the benefit under 35 USC 119(e) of U.S. Provisional Application No. 62/475,654, filed on Mar. 23, 2017, both of which are incorporated herein by reference in their entirety.

FIELD OF THE INVENTION

The present invention provides buthionine sulfoximine (BSO) for use as a medicament with a metallodrug, methods of treatment using BSO and a metallodrug, kits comprising BSO and a metallodrug, and compositions comprising BSO and a metallodrug.

BACKGROUND

Reduction of immune activation represents a promising frontier for development of novel therapeutics for cancer and HIV/AIDS. These diseases are characterized by malignant immune hyperactivation linked to immune exhaustion. Especially in the context of HIV/AIDS, however, therapeutic interventions aimed at blocking immune hyperactivation have produced mixed or limited results in clinical settings (Shytaj and Savarino, 2015).

A new emerging wave of research in anticancer therapy exploits oxidative stress and nitrosative stress produced by metallodrugs, such as gold(I)-containing metallodrugs and platinum(II)-containing metallodrugs. Other groups of metallodrugs which are thought to be useful are gold(III)-containing metallodrugs and platinum(IV)-containing metallodrugs. Indeed, cisplatin, a platinum(II)-containing metallodrug, is currently used as a chemotherapeutic agent. In addition, auranofin, a gold-containing metallodrug, has been shown to be useful in the treatment of rheumatoid arthritis, and has been considered in anticancer strategies.

A further area of research has been the combination of metallodrugs with other pharmaceuticals to potentiate oxidative stress. There are two main cellular anti-oxidative pathways, i.e. the thioredoxin (Trx)/thioredoxin reductase (TrxR) system and glutathione (GSH). These machineries are in part overlapping and are capable of backing each up other (Benhar et al. JCI 2016). In case one of the two systems is blocked, the other may become up-regulated, thus providing at least partial compensation for the intracellular antioxidant machinery. Some metallodrugs, and particularly gold-containing compounds, such as auranofin, are known to inhibit TrxRs. In addition, metallodrugs have been shown to selectively kill cells derived from multiple types of cancers when administered in the presence of buthionine sulfoximine (BSO). BSO inhibits gamma-glutamyl cysteine synthetase, a limiting enzyme in the glutathione synthetic pathway (Griffith et al. J Biol Chem. 1979), and therefore inhibits the other of the two anti-oxidative pathways. Thus, the possibility of combining a metallodrug, such as auranofin and cisplatin, with BSO for treating diseases might be useful through a) the ability to induce oxidative and nitrosative stress, and b) the ability to counteract the cellular oxidative machinery which activates in order to limit the effects of oxidative stress.

Malaker et al. studied the effect of BSO, including sub-micromolar concentrations, on glutathione levels following glutathione depletion by diethylmaleate. This study was conducted with a view to use BSO in anticancer treatment with etanidazole, in order to radiosensitize cells (Malaker et al. Int J Radiat Oncol Biol Phys. 1994). In order to achieve a 90% decrease in glutathione levels, 6 µM BSO was required, and the authors also reported a possible problem with under-dosing of BSO.

BSO has been used in the treatment of cancer, particularly neuroblastoma, in combination with melphalan. For example, Villablanca et al. (2016) administered a 3 $g/m^2$ bolus, followed by 24 $g/m^2$/day of BSO with escalating doses of melphalan (20-125 $mg/m^2$) to patients with recurrent or resistant high-risk neuroblastoma.

Anderson et al. (2015) administered BSO as a fixed loading dose of 3 $g/m^2$ followed by a 72-hour continuous infusion of 0.75 $g/m^2$ or 1 $g/m^2$, with 15 mg/m2 of melphalan, in order to determine the effect for children with recurrent or refractory high-risk neuroblastoma.

O'Dwyer et al. (1992) administered 1.5 $g/m^2$ BSO at 12 hour intervals for six doses, alone or with 15 $mg/m^2$ melphalan after the fifth dose. Marked depletion of cellular GSH was noted.

From in vitro experiments, the combination of gold(I)-containing compounds, such as auranofin, and BSO is known to limit immune activation (Vint et al., 1993), but the effects of this drug combination on immune activation in the in vivo cancer setting have, however, remained unexplored. Using a mathematical model it has been possible to predict that limitation of immune activation might lead to a "bottleneck effect" which can favor the maintenance of immune responses that are more "focused" towards the antigens less likely to be mutated. These antigens are statistically more represented in a typical viral population due to their being more evolutionary conserved and, thus, the lymphocytic clones targeting them are more likely to be overrepresented and survive the aforementioned "bottleneck effect" (Benhar et al. JCI 2016). Thus, it appears that induction of an efficient immune response through lymphorestriction could have played a pivotal role in the therapeutic effects of auranofin and BSO in the in vivo studies conducted so far. The availability of manageable agents able to counteract malignant immune hyperactivation in cancer represents a new research priority.

BSO in combination with platinum-containing metallodrugs, such as cisplatin, for the treatment of cancer, has also been explored. Cisplatin is a chemotherapeutic agent, used for treating, for example, malignant mesothelioma, bladder, ovarian, testicular, non-small cell lung, endometrial, penile, head and neck, anal, biliary tract, hepatocellular and gastric cancer, non-Hodgkin's lymphoma, malignant melanoma and neuroblastoma, amongst others. Dosages up to 100 $mg/m^2$ are considered safe (Prescriber's Digital Reference—cisplatin; http://www.pdr.net/drug-summary/Cisplatin-cisplatin-1472).

Tsutsui et al. (1986) administered 5 mmol/kg (equivalent to 111.5 mg/kg) BSO 12 hours before administration of cyclophosphamide, cisplatin or bleomycin. Cisplatin was administered at an amount of 2.5, 5, 7.5 or 10 mg/kg. It was found that BSO increased the anti-cancer effects of these three chemotherapeutic agents.

Saikawa et al. (1993) aimed to evaluate the enhancement of the antitumor activity of cisplatin by BSO in vitro and in vivo. In vitro, pre-treatment of MKN-28 and MKN-45 cells with BSO (5, 10 and 25 mM) increased the antitumor activity of cisplatin (0.1, 0.3, 1.0 and 3.0 µg/ml for MKN-28 and 0.01, 0.1, 0.3 and 1 µg/ml for MKN-45). In vivo, antitumor effects of cisplatin (6 or 9 mg/kg) were enhanced by pre-treatment with BSO, which was administered intraperitoneally at a dose of 500 mg/kg.

Similarly to neoplastic conditions, infections by lentiviruses (a viral genus comprising human immunodeficiency virus (HIV)) appear to be susceptible to the auranofin/BSO combination, and the administration of auranofin (0.4 mg/kg/day) and BSO (450 mg/kg) to macaques infected with the HIV homolog SIVmac251 in combination with antiretroviral therapy (ART) induced a functional cure of the disease following suspension of all therapies (Shytaj et al. Retrovirology 2013; Shytaj et al. J Virol. 2015).

This functional cure consisted of prolonged control of viral load for up to two years: the macaque that was not subjected to euthanasia has remained healthy and in good condition four and a half years after suspension of therapy. This functional cure was associated with higher HIV-specific responses than those observed in auranofin/BSO-untreated macaques in which ART had been suspended. In the case of HIV, not only can limitation of immune activation result in increased immune responses, but also in a decrease of the main HIV reservoir, i.e. latently infected memory $CD4^+$ T-cells harboring silent copies of the viral DNA which cannot be attacked by drugs or recognized by the immune system. Similarly to cancer cells, these cells proliferate within the organism despite the high-level suppression of viral replication provided by ART (Benhar et al. JCI 2016). There is a correlation between the magnitude of the viral reservoir and the level of immune activation in HIV-infected individuals (Shytaj and Savarino Retrovirology 2015). Immune activation per se represents a problem in ART-treated $HIV^+$ individuals, as high levels thereof are associated with a higher incidence of non-AIDS defining events, such as cardiovascular disease and cancer. Strategies aimed at limiting immune activation during ART are a so far unmet medical need.

Auranofin has been used for decades in treatment of rheumatoid arthritis, a condition in which it showed some degree of efficacy, according to meta-analysis studies (Suarez-Almazor et al. Cochrane Database Syst Rev. 2000). However, one limitation of its use resides in the fact that, for safety, the drug cannot be administered for periods longer than nine months. Moreover, doses greater than 9 mg/day are considered unsafe, as they can cause gold toxicity (Prescriber's Digital Reference—Auranofin; http://www.pdr.net/drug-summary/Ridaura-auranofin-795). It is, therefore, highly desirable to increase its therapeutic potency during the treatment period, and BSO is considered to be an additive option to auranofin. However, the use of BSO is limited by the costs and complexity of its synthesis (an explosive step is involved in the synthetic pathway; Griffith et al. J Biol Chem. 1979) and by the extremely high dosages adopted so far in vivo (Bailey et al. J Clin Oncol. 1994, O'Dwyer et al. J Clin Oncol. 1996, Bailey et al. J Natl Cancer Inst. 1997; Anderson et al. Pediatr Blood Cancer. 2015). While these dosages result in peak plasma drug concentrations matching those at which the best in vitro effects have been documented (Meister. Pharmacol Ther. 1991; Vint et al. Cell. Immunology 1993; Shytaj et al. J. Virol 2015), they increase the risk of side effect and the problems with producing enough BSO for clinical use, as shown by the very long hiatus between clinical trials of this drug.

BSO has previously been reported to decrease glutathione when administered in the low micromolar concentration range; however, more profound glutathione depletion has been observed at higher concentrations, a phenomenon which has prompted investigators to test the drug in vivo at dosages resulting in massive glutathione depletion (by approx. 80%), in order to maximize the chances for success, as discussed above. As also discussed above, high BSO concentrations (up to the millimolar range) have also been largely adopted in in vitro experiments aimed at chemosensitising cells to antineoplastic and anti-HIV latency agents. Accordingly, high dosages (namely, inducing peak plasma concentrations of 250 µM) of BSO have been previously specified.

Wang et al. (Oncotgarget 2017) explored the potential anticancer application of a combination of low dose/concentration BSO (producing a peak plasma concentration of 1 µM) and auranofin. However, the decrease in the concentration of BSO to the low micromolar range was compensated by an increase of auranofin to concentrations which were far superior 6-fold) to those acceptable in a clinical setting, and at which auranofin has off-target effects, including BSO-like induction of a decrease in glutathione levels (You et al. Molecular Medicine Reports 2015). Moreover, in the highly resistant murine mammary carcinoma cell line that they adopted, Wang et al. were not able to detect any directly cytotoxic/anticancer effect of the auranofin/submicromolar BSO combination, and analysed the aforementioned drug combination in terms of radiosensitization of tumor cells. The chemosensensitisation of the cells, by the drug combination, to the cytotoxic effects of a metallodrug at clinically-acceptable concentrations was not analysed.

So far, therefore, it is considered that high therapeutic dosages of BSO are required for treatment with metallodrugs, or that high doses of metallodrugs are required to compensate for any low dosages of BSO. Indeed, it has been considered that low dosages of BSO have an opposite effect to metallodrugs. For example, Mayer et al. showed that BSO could reduce the nephrotoxicity of the metallodrug cisplatin in rats (Mayer et al. J. Cancer Res. Clin. Oncol. 1989). Therefore, the interest in an anticancer combination of a metallodrug and BSO has decayed throughout the years despite promising results in vitro and in vivo.

Thus, there is a need to provide a treatment which overcomes the problems and disadvantages discussed above. In particular, it is desirable to provide a treatment which overcomes the problem of off-target effects, malignant immune hyperactivation and inefficient immune responses. It is also desirable to overcome the problem of the cost and complexity of production of BSO, and inconvenient treatment regimes.

SUMMARY OF THE INVENTION

The present invention provides solutions to the problems discussed above because it has now, surprisingly, been found that dosages of BSO 10-1000-fold lower than previously used, together with clinically-acceptable amounts of metallodrugs, are useful for killing cancer cells and sensitising cancer cells to chemotherapeutic agents, for limiting malignant immune hyperactivation and for improving the efficiency of immune responses. Thus, the ratio of BSO to metallodrug can be decreased, and the possibility of off-target effects in patients can be limited.

The decreased dosages of BSO provide for the treatment of diseases through an anti-inflammatory effect involving the reduction of immune hyperactivation, or through a direct cytotoxic effect. For example, the reduced dosages of BSO of the present invention have the potential to limit the proliferation of HIV reservoir cells. The reduced dosages of BSO also provide a direct effect on targets of the immune system, in particular, killing and chemosensitising of cancer cells. BSO can be administered separately, sequentially or simultaneously with the metallodrug. Thus, the cost of treatments using BSO can be reduced, and the complexity of the production of BSO can be mitigated. Moreover, the reduction in the amount of BSO means that BSO and a metallodrug could be provided in a single composition, thereby reducing the inconvenience of treatment to the patient and providing further, more convenient, routes of administration.

The present invention also relates to methods of treating patients with BSO and a metallodrug, to kits comprising BSO and a metallodrug, and to compositions comprising BSO and a metallodrug. The methods, kits and compositions, provide for BSO to be administered at a dosage as described above, namely, 10-1000-fold lower than previously used dosages.

Thus, the invention provides BSO for use in a method of treatment, separately, simultaneously or sequentially with a clinically-acceptable amount of a metallodrug, wherein the method comprises administering BSO at an amount 10-1000-fold lower than previously used.

The invention also provides BSO for use in a method of treatment of cancer, HIV or a rheumatic disease, wherein the method comprises administering (a) BSO at a dosage of less than or equal to 50 mg/kg, and (b) a metallodrug at a clinically-acceptable dosage.

The treatment may be of cancer, and the BSO may be administered at a dosage of less than or equal to 9 mg/kg.

In particular, the cancer may be haematological malignancy, Hodgkin's lymphoma, non-Hodgkin's lymphoma, lung carcinoma, prostate cancer, hepatocellular carcinoma, breast cancer, glioblastoma, uterine cervix carcinoma or Kaposi's sarcoma.

The BSO may be administered at a dosage of between 0.45 mg/kg and 9 mg/kg. Alternatively, the treatment may be of HIV or a rheumatic disease.

In particular, the treatment may be of rheumatic arthritis or lupus.

The BSO may be administered at a dosage of between 0.45 mg/kg and 45 mg/kg.

The metallodrug may comprise a gold-containing metallodrug and/or a platinum-containing metallodrug.

The treatment may be for rheumatic diseases or HIV, and the metallodrug comprises a gold-containing metallodrug.

The gold-containing metallodrug may comprise auranofin, aurothioglucose, sodium aurothiopropanolsulfonate and/or aurothiomalate, and/or the platinum-containing metallodrug comprises cisplatin, carboplatin, oxaliplatin, nedaplatin, lobaplatin, heptaplatin and/or satraplatin.

The gold-containing metallodrug may comprise auranofin, aurothioglucose, sodium aurothiopropanolsulfonate and/or aurothiomalate, and preferably may be auranofin.

The ratio of BSO to gold-containing metallodrug may be 1:0.25 to 1:10, and/or the ratio of BSO to platinum-containing metallodrug may be 1:5 to 1:25.

Preferably, the treatment is of cancer and the ratio of BSO to gold-containing metallodrug is 1:1 to 1:10 and/or the ratio of BSO to platinum-containing metallodrug is 1:5 to 1:25.

Alternatively, the treatment may be of HIV or a rheumatic disease, and the ratio of BSO to gold-containing metallodrug may be 1:0.25 to 1:1.

Preferably, the metallodrug comprises auranofin administered at a dosage of 3-9 mg/day.

Alternatively, the treatment is of cancer and the metallodrug comprises cisplatin administered at a dosage of less than or equal to 100 mg/m$^2$.

The invention also provides a method of treating cancer, HIV or a rheumatic disease, wherein the method comprises administering to a patient in need thereof (a) BSO at a dosage of less than or equal to 50 mg/kg, and (b) a metallodrug at a clinically-acceptable dosage.

The invention further provides a method of treatment of cancer, HIV or a rheumatic disease, wherein the method comprises administering to a patient in need thereof (a) BSO at a dosage sufficient to achieve a peak plasma concentration of 0.5-20 µM, and (b) a metallodrug at a clinically-acceptable dosage.

Preferably, the BSO is administered at a dosage sufficient to achieve a mean plasma concentration of 0.05-2 µM.

The method may be for the treatment of HIV or a rheumatic disease.

Alternatively, the method is for the treatment of cancer and the BSO is administered at a dosage sufficient to achieve a mean plasma concentration of 0.05-0.8 µM.

The invention also provides a kit comprising BSO and a metallodrug, wherein (a) the BSO is at a dosage of less than or equal to 5000 mg, and (b) the metallodrug is at a clinically-acceptable dosage.

The invention further provides a kit comprising BSO and a metallodrug, wherein the metallodrug is at a clinically-acceptable dosage, and the ratio of the BSO to the metallodrug in the kit is between 1:0.25 and 1:25.

The invention also provides a pharmaceutical composition comprising BSO and a metallodrug, wherein the metallodrug is present at a clinically-acceptable amount, and the BSO is present at a dosage of less than or equal to 50 mg/kg, and wherein the pharmaceutical composition comprises a pharmaceutically-acceptable carrier, diluent and/or excipient.

The invention further provides a pharmaceutical composition comprising BSO and a metallodrug, wherein the metallodrug is present at a clinically-acceptable amount and the ratio of BSO to the metallodrug is between 1:0.25 and 1:25, and wherein the pharmaceutical composition comprises a pharmaceutically-acceptable carrier, diluent and/or excipient.

"Clinically-acceptable amount", as used herein, means an amount which is recognised as being safe by the relevant medical authorities. Guidance on clinically-acceptable dosages can be found, for example, at the Prescriber's Digital Reference (http://www.pdr.net/).

A "metallodrug", as used herein, is a pharmaceutical which contains a metal as an active ingredient, for example, silver, zinc, platinum or gold. They are commonly used as anti-cancer and antimicrobial drugs. Metallodrugs are well-known in the art and include gold-containing, platinum-containing, silver-containing and zinc-containing drugs. Specific metallodrugs include cisplatin, auranofin, carboplatin and silver sulfadiazine.

"Mean plasma concentration", as used herein means the average plasma concentration, calculated as Area Under the Curve of a concentration-time curve after a single dose or in steady state.

"Peak plasma concentration", as used herein, means the highest plasma concentration of a drug achieved after administration of the drug.

DETAILED DESCRIPTION

The present invention is based on the discovery that it is possible to achieve the same, if not improved, therapeutic effects in the treatment of patients by using concentrations of BSO that are much lower than previously used, together (separately, simultaneously or sequentially) with a clinically-acceptable amount of a metallodrug. The invention relates, in general terms, to the use of concentrations of BSO which are much lower than previously used, and a metallodrug, for treating patients. In particular, the dosages of BSO of the present invention are 10-1000-fold lower than previously used, and this allows the ratio of BSO to metallodrug to be increased.

Figure 4:
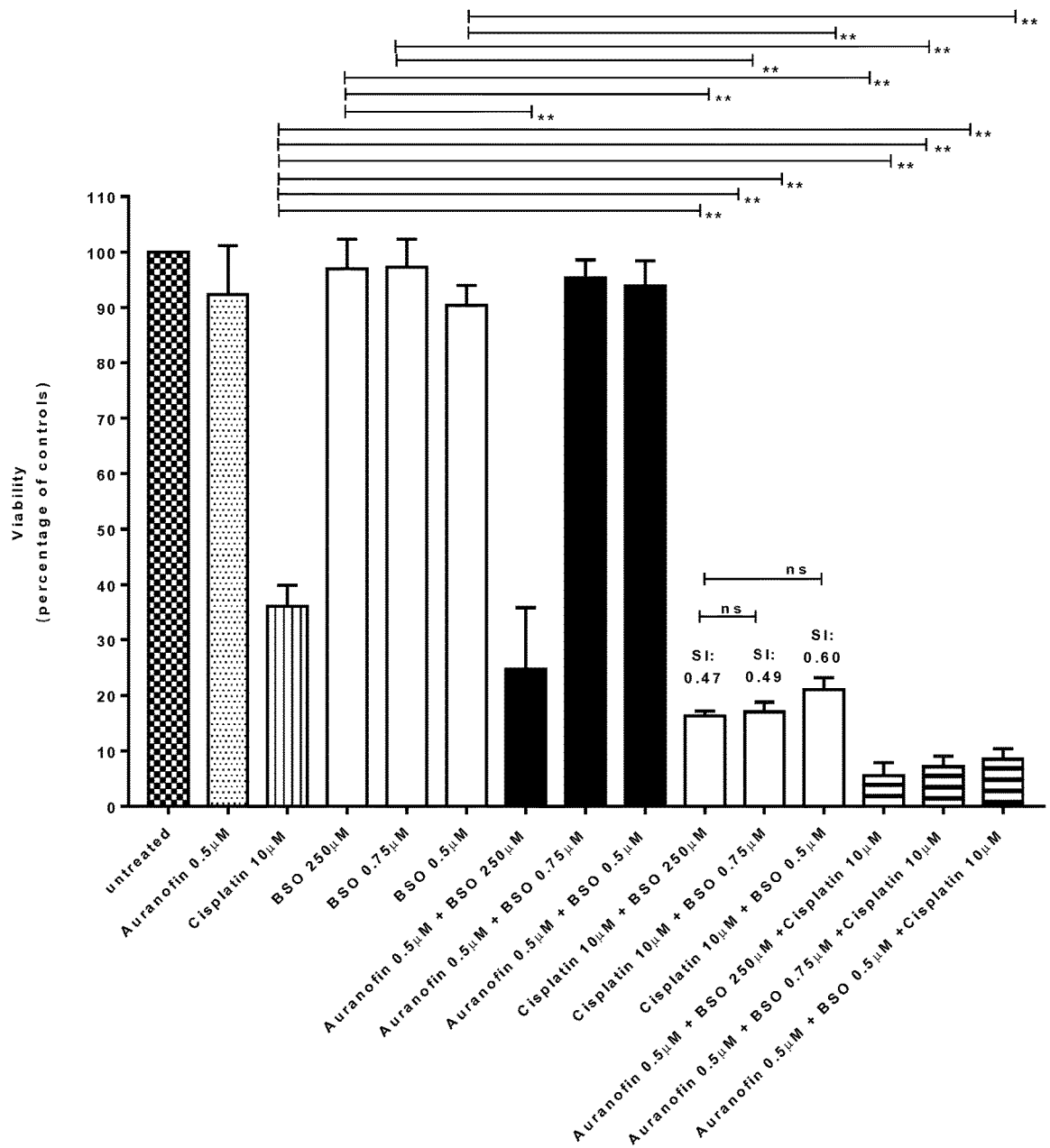
FIG. 4 is a graph showing the viability of Jurkat T-cells treated with different concentrations of cisplatin, auranofin and/or buthionine sulfoximine (BSO). Viability was measured 48 hours after treatment with the drugs at the indicated concentrations with the MTT assay. Absorbance values were normalized over untreated controls and expressed as percentage. Concentrations are expressed in μM. Data are expressed as mean±SEM and were. Asterisks show the significant differences [*q<0.05; **q<0.01; q is the P value corrected for multiple comparisons by controlling the False Discovery Rate (threshold for significance=q=0.05)]. NS: non-significant. The synergistic index (SI) is expressed where significant differences exist in comparison with the single drug treatments.
Figure 5:
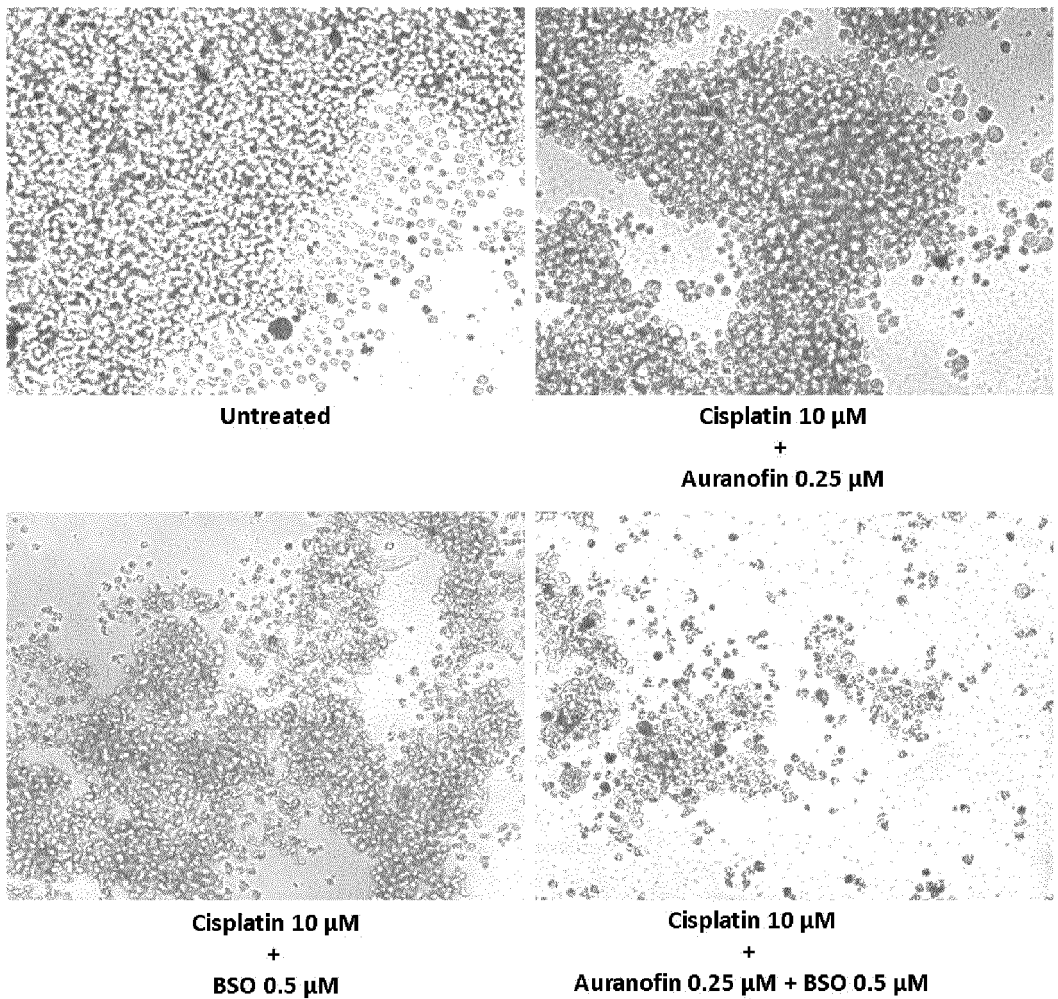
FIG. 5 is microphotographs of Jurkat T-cells treated with different concentrations of cisplatin, auranofin or buthionine sulfoximine (BSO).

Indeed, Example 1 shows that reduced concentrations of BSO, with a metallodrug at a clinically-acceptable dosage, have a limiting effect on immune activation and have an anti-proliferative effect. As discussed in Example 1, the reduction of the peak plasma concentration of BSO to 2 μM, with a clinically-acceptable dosage of a metallodrug, limited cell viability to a similar degree to previously used peak plasma BSO concentrations of 250 μM. Submicromolar concentrations of BSO were also shown to have a direct anti-cancer effect (FIGS. 2 and 3), and a synergism (indicated by a synergistic index of less than 0.9) was measured only for BSO concentrations in the submicromolar range. The BSO concentrations of the invention were also shown to induce morphological changes which are linked to poor cell viability (FIG. 3). Similar effects were seen using cisplatin instead of auranofin, at a clinically-acceptable dosage (FIGS. 4 and 6), and the anticancer effect was similar to that produced by a concentration of BSO three orders of magnitude higher. Furthermore, it was found that BSO at concentrations 10-1000-fold lower than previously used produced an increased antineoplastic effect when used with both auranofin and cisplatin (FIGS. 4 and 5).

The results of Examples 2 and 3 also show that concentrations of BSO in the low micromolar or submicromolar concentration range, and in combination with auranofin, may well have an impact on the viral reservoir (for example, in HIV) which is at least similar to that achieved by previously-used dosages.

BSO is administered to the patient at dosage 10-1000 times lower than the dosages currently used or postulated. In particular, BSO is given at a dosage of less than or equal to 45 mg/kg. In some embodiments, BSO is administered at a dosage of less than or equal to 40 mg/kg, 35 mg/kg, 30 mg/kg, 25 mg/kg, 20 mg/kg, 15 mg/kg, 10 mg/kg, 9 mg/kg, 8 mg/kg, 7 mg/kg, 6 mg/kg, 5 mg/kg, 4 mg/kg, 3 mg/kg, 2 mg/kg, 1 mg/kg, 0.9 mg/kg, 0.8 mg/kg, 0.7 mg/kg, 0.6 mg/kg, 0.5 mg/kg, 0.45 mg/kg, 0.4 mg/kg, 0.35 g/kg, 0.3 mg/kg, 0.25 mg/kg, 0.2 mg/kg, 0.15 mg/kg or 0.1 mg/kg.

In some embodiments, BSO is administered at a dosage of at least 0.1 mg/kg, 0.15 mg/kg, 0.2 mg/kg, 0.25 mg/kg, 0.3 mg/kg, 0.35 mg/kg, 0.4 mg/kg, 0.45 mg/kg, 0.5 mg/kg, 0.6 mg/kg, 0.7 mg/kg, 0.8 mg/kg 0.9 mg/kg or 1.0 mg/kg.

In preferred embodiments, BSO is administered at a dosage between 0.45 mg/kg and 45 mg/kg. In other preferred embodiments, BSO is administered at a dosage of between 0.45 mg/kg and 9 mg/kg. In some embodiments, BSO is administered at a dosage of between 0.45 mg/kg and 8 mg/kg.

The dosage of BSO can also be expressed in terms of the peak or mean plasma concentration to be achieved by the administration of BSO. Techniques for measuring the peak and mean plasma concentration are well known to the person skilled in the art. In particular, the peak and mean plasma concentrations of a drug are determined by measuring plasma levels of the drug at set times after administration of the drug, for example, every hour from time zero to 24 hours after administration. Plasma concentration-time profiles are plotted. Mean plasma concentration is determined by calculating the area under the profile (Area Under Curve; AUC) using the trapezoidal rule. Peak plasma concentration is the highest plasma concentration achieved after a single dose of the drug. Plasma concentration of drugs can be measured by well-known techniques, such as capillary electrophoresis/HPLC (Sandor et al., 1995) and inductively-coupled plasma-mass spectrometry (ICP-MS; Capparelli et al., 2017).

In some embodiments, BSO is administered at a dosage which achieves a peak plasma concentration of less than or equal to 25, 20, 15, 10, 5, 4, 3, 2, 1, 0.9, 0.8, 0.7, 0.6, 0.5, 0.4, 0.3, 0.25, 0.2, 0.15, 0.1 or 0.05 $\mu$M. In some embodiments, the peak plasma concentration is greater than or equal to 0.05, 0.1, 0.15, 0.2, 0.25, 0.3, 0.4, 0.5, 0.6, 0.7, 0.8, 0.9, 1, 2, 3, 4, 5, 10, 15, and 20 $\mu$M. In some embodiments, the peak plasma concentration is less than 2 $\mu$M or less than 1 $\mu$M. In other embodiments, the peak plasma concentration is 0.5-20 $\mu$M.

In some embodiments, BSO is administered at a dosage which achieves a mean plasma concentration of less than or equal to 25, 20, 15, 10, 5, 4, 3, 2, 1, 0.9, 0.8, 0.7, 0.6, 0.5, 0.4, 0.3, 0.25, 0.2, 0.15, 0.1 or 0.05 $\mu$M. In some embodiments, the mean plasma concentration is greater than or equal to 0.05, 0.1, 0.15, 0.2, 0.25, 0.3, 0.4, 0.5, 0.6, 0.7, 0.8, 0.9, 1, 2, 3, 4, 5, 10, 15, and 20 $\mu$M. In some embodiments, the mean plasma concentration is less than 2 $\mu$M or less than 1 $\mu$M. In other embodiments, the peak plasma concentration is 0.05-2 $\mu$M. In further embodiments, the peak plasma concentration is 0.05-0.8 $\mu$M.

The metallodrug used in the present invention may be any metallodrug. In particular, metals, and particularly transition metals, are able to induce oxidative stress through the formation of reactive oxygen species (ROS). They are also able to produce nitrosative stress through the generation of reactive nitrogen species (RNS). It is thought that this oxidative and/or nitrosative stress can be potentiated by the inhibition of cellular anti-oxidative pathways, such as the inhibition GSH by BSO, as glutathione is one of the main scavengers of ROS. Furthermore, some heavy metals being used and explored in pharmacotherapy (i.e. gold, platinum, silver, ruthenium and silver) are able to inhibit the Trx/TrxR anti-oxidative pathway, further potentiating the oxidative and/or nitrosative stress induced by metallodrugs. Thus, of the decreased dosages of BSO of the invention (i.e. which provides as increased ratio of BSO to metallodrug) maintains the potentiation of the effect of ROS while reducing the amount of off-target side effects caused by BSO.

Interestingly, the ratios of BSO to auranofin or cisplatin (detailed further below) that can be achieved with the present invention overlap, such that it would be expected that BSO will exert synergistic effects in combination with other metallodrugs, particularly those which are capable of exerting pro-oxidant effects by similar mechanisms, and more particularly, other gold- or platinum-containing drugs, at similar molar ratios.

In some embodiments, BSO is administered in combination with a metallodrug, such as a gold-containing, a silver-containing, a zinc-containing and/or a platinum-containing drug. Examples of gold-containing metallodrugs which may be used are auranofin, aurothioglucose, sodium aurothiopropanolsulfonate and aurothiomalate. Examples of platinum-containing metallodrugs which may be used are cisplatin, carboplatin, oxaliplatin, nedaplatin, lobaplatin, heptaplatin and/or satraplatin. In some embodiments, the metallodrug is auranofin or cisplatin.

In some embodiments, more than one metallodrug may be used. For example, more than one gold-containing metallodrug, more than one platinum-containing drug, more than one zinc-containing metallodrug, or more than one silver-containing metallodrug may be used. In some embodiments, the more than one metallodrug may be a combination of one or more gold-containing metallodrug, one or more platinum-containing drug, one or more zinc-containing metallodrug and/or one or more silver-containing metallodrug. Thus, in some embodiments, the metallodrug is one or more of auranofin, aurothioglucose, sodium aurothiopropanolsulfonate, aurothiomalate, cisplatin, carboplatin, oxaliplatin, nedaplatin, lobaplatin, heptaplatin and/or satraplatin. In some embodiments, a gold-containing metallodrug and a platinum-containing metallodrug are used. Preferably, auranofin and cisplatin are used.

The metallodrug is administered at a clinically-acceptable amount. In particular, the use of metallodrugs for the treatment of diseases, and maximum dosages thereof that are considered safe, are well known. For example, as mentioned above, gold-containing metallodrugs such as auranofin are considered unsafe at dosages greater than 9 mg/day (Prescriber's Digital Reference—Auranofin; http://www.pdr.net/drug-summary/Ridaura-auranofin-795). In embodiments where more than one metallodrug is used, the dosage of each metallodrug is a clinically-acceptable dosage.

Thus, for example, in embodiments comprising auranofin, the dosage is less than or equal to 9 mg/day. In other embodiments the dosage of auranofin is 3-9 mg/day or 3-6 mg/day. The dosage of auranofin may result in a mean plasma concentration of less than or equal to 3 $\mu$M, 2 $\mu$M or 1 $\mu$M. Preferably, the dosage of auranofin results in a mean plasma concentration of less than 1 $\mu$M. In some embodiments, the auranofin is administered at a dosage sufficient to achieve a mean plasma concentration of 0.2-1 $\mu$M.

In embodiments comprising cisplatin, the clinically-acceptable dosage is less than or equal to 100 mg/m$^2$ (Prescriber's Digital Reference—cisplatin; http://www.pdr.net/drug-summary/Cisplatin-cisplatin-1472). In other embodiments, the dosage of cisplatin is less than or equal to 75, 70, 65, 60, 55, 50, 45, 40, 35, 30 or 25 mg/m$^2$. In some embodiments, cisplatin is administered at a dosage sufficient to achieve a mean plasma concentration of less than or equal to 50, 40, 30, 20, 10 or 5 $\mu$M. In some embodiments, cisplatin is administered at a dosage sufficient to achieve a mean plasma concentration of 2-50 $\mu$M. In other embodiments, cisplatin is administered at a dosage sufficient to achieve a mean plasma concentration of 2-30 $\mu$M. In some embodiments, cisplatin is administered at a dosage sufficient to achieve a peak plasma concentration of 30-50 $\mu$M.

In embodiments where both auranofin and cisplatin are used, the dosage of auranofin is as described above, and the dosage of cisplatin is as described above.

In some embodiments, the dosage of BSO and the metallodrug can be defined as a ratio, wherein the amount of the metallodrug remains as a clinically-acceptable amount. In the present invention, the ratio of BSO to metallodrug is decreased by reducing the amount of BSO 10-1000-fold. In some embodiments, the ratio of BSO to metallodrug is 1:0.25 to 1:25. In some embodiments, the ratio of BSO to metallodrug is 1:0.25 to 1:13, 1:0.25 to 1:10, 1:0.25 to 1:5, 1:0.25 to 1:1, 1:0.25 to 1:0.5. In some embodiments, the ratio of BSO to metallodrug is 1:1 to 1:2, 1:3, 1:4, 1:5, 1:6, 1:7, 1:8, 1:9 or 1:10. In some preferred embodiments, the metallodrug is a gold-containing metallodrug and the ratio of BSO to metallodrug is 1:1 to 1:10. In such embodiments, the gold-containing metallodrug may be auranofin. In other embodiments, the metallodrug may be a gold-containing metallodrug and the ratio of BSO to metallodrug is 1:0.25, 1:0.5 or 1:1. In such embodiments, the gold-containing metallodrug may be auranofin. In some embodiments, the metallodrug is a platinum-containing metallodrug and the ratio of BSO to metallodrug is 1:5 to 1:25, or, more preferably, 1:13 to 1:25. In such embodiments, the platinum-containing metallodrug may be cisplatin.

In some embodiments, two or more metallodrugs can be administered with BSO, and the ratio of each metallodrug to BSO may be as defined above. In some embodiments, the ratio of BSO to a first metallodrug to a second metallodrug is 1:1-13:5-25. In some embodiments, BSO is administered with auranofin and cisplatin, and the ratio of BSO to auranofin to cisplatin is 1:1-3:5-25.

BSO and a metallodrug are useful for treatment via an anti-inflammatory effect and/or a cytotoxic effect. In particular, the anti-inflammatory effect involves a reduction in immune hyperactivity. An anti-inflammatory effect can be determined, for example, by measuring lymphocyte activation markers such as the percentage of CD38+HLADR+ CD8+ T-cells. A cytotoxic effect can be determined, for example, by measuring neoplastic mass. In the case of HIV, the cytotoxic effect can be determined, for example, by measuring the amount of HIV DNA in peripheral blood mononuclear cells.

BSO and the metallodrug can be used for the treatment of cancer, rheumatic diseases or HIV, amongst others. Either, or both, the cytotoxic effect and the anti-inflammatory effect can be used to treat cancer. Rheumatic diseases and HIV are treated via the anti-inflammatory effect. In some embodiments, the cancer is a hematological malignancy, Hodgkin's or non-Hodgkin lymphoma, lung carcinoma, prostate cancer, hepatocellular carcinoma, breast cancer, glioblastoma, uterine cervix carcinoma, or Kaposi's sarcoma. The rheumatic disease may be rheumatic arthritis or lupus. HIV may be HIV-1.

As discussed above, the metallodrug is administered at a clinically-acceptable amount, and this also includes the selection of an appropriate metallodrug for treating the disease in question. Thus, in some embodiments, the disease to be treated is cancer and the metallodrug is a gold-containing metallodrug, a platinum-containing metallodrug, a zinc-containing metallodrug and/or a silver-containing metallodrug. Preferably, the metallodrug is a gold-containing metallodrug and/or a platinum-containing metallodrug. In such embodiments, the metallodrug may be cisplatin, carboplatin, oxaliplatin, nedaplatin, lobaplatin, heptaplatin, satraplatin, auranofin, aurothioglucose, sodium aurothiopropanolsulfonate and/or aurothiomalate. In preferred embodiments, the metallodrug is cisplatin and/or auranofin. In other embodiments, the disease to be treated is a rheumatic disease or HIV, and the metallodrug is a gold-containing metallodrug.

In some embodiments, BSO is used, with a metallodrug, for treatment via the cytotoxic effect. The disease to be treated via the cytotoxic effect may be cancer. In some embodiments of treatment via the cytotoxic effect, BSO is administered at a dosage of 0.45-9 mg/kg, and the metallodrug is administered at a clinically-acceptable amount. The dosage of the BSO may be such as to achieve a mean plasma concentration of 0.05-0.8 µM when administered to the patient. In some embodiments, the metallodrug is auranofin. In such embodiments, the ratio of BSO to auranofin may be 1:1 to 1:10. In other embodiments, the metallodrug is cisplatin. In these embodiments, the ratio of BSO to cisplatin may be 1:5 to 1:25. In other embodiments, the ratio of BSO to cisplatin is 1:13 to 1:25. In some embodiments, the metallodrug is auranofin and cisplatin, and the ratio of BSO to auranofin to cisplatin is 1:1-10:5-25.

In some embodiments, BSO is used, with a metallodrug, for treatment via the anti-inflammatory effect. In some such embodiments, BSO is administered at a dosage of 0.45-45 mg/kg, and the metallodrug is administered at a clinically-acceptable amount. The dosage of the BSO may be such as to achieve a mean plasma concentration of 0.05-2 µM. In some embodiments, the metallodrug is auranofin. In some embodiments, the ratio of BSO to auranofin is 1:0.25 to 1:1, preferably 1:0.25. In some embodiments, cancer, a rheumatic disease or HIV, such as those described above, is treated via the anti-inflammatory effect.

BSO can be used, with a metallodrug, together with existing therapies for the disease in question. Thus, in some embodiments, BSO and a metallodrug can be used together with an optimised background therapy, which may be an optimised background therapy for cancer, HIV or a rheumatic disease. In some embodiments, BSO is administered in cycles, intertwined with periods of treatment with optimised background therapy and/or a metallodrug. The use of BSO may comprise a structured treatment interruption (STI) involving the interruption of administration of all treatments with the optimised background therapy and/or the metallodrug. In some embodiments, the BSO is administered in cycles and the STI is at the end of the final cycle of BSO administration.

In embodiments where the BSO and metallodrug are used to treat HIV, the patient may be receiving antiretroviral therapy (ART).

The invention also provides a method of treating a patient in need thereof with BSO and a metallodrug. The BSO and the metallodrug may be administered separately, simultaneously or sequentially. The BSO is administered at a dosage less than or equal to 50 mg/kg, or any other dosage described above. The metallodrug is administered at a clinically-acceptable dosage, as described above. The BSO and the metallodrug may be administered at a dosage ratio described above. The method of treatment may be for the treatment of a patient via the cytotoxic effect of BSO with a metallodrug, or via the anti-inflammatory effect of BSO with a metallodrug, as described above. In particular, the method of treatment may be for the treatment of cancer, a rheumatic disease or HIV.

The invention also provides a kit comprising BSO and a metallodrug. The kit is for administering BSO and a metallodrug as described above. Thus, the kit comprises BSO at a dosage of less than or equal to 5000 mg, and a metallodrug at a clinically-acceptable dosage. The dosages of the BSO and the metallodrug in the kit are such that the ratio of BSO to metallodrug in the kit is a ratio disclosed above, when the metallodrug is at a clinically-acceptable dosage. The kit allows for the administration of BSO at a dosage of less than or equal to 50 mg/kg, or any other dosage as described above. The dosage of the metallodrug, in the kit, may also be in accordance with the dosages described above. The kit is useful for the treatment of cancer, rheumatic diseases and HIV, as described above.

The invention also provides for a composition comprising both BSO and a metallodrug, and a pharmaceutically-acceptable carrier, diluent and/or excipient. Such pharmaceutically-acceptable carriers, diluents and excipients are known to those skilled in the art. The composition provides for simultaneous administration of both BSO and the metallodrug, in a single dosage form. In some embodiments, the BSO and the metallodrug are present in a single solution. In some embodiments, the BSO and metallodrug are present in a solid form. The solid form may be reconstituted before administration to the patient. In some embodiments, the composition is administered by continuous infusion.

The amounts of BSO and the metallodrug in the composition are as described above. Thus, the composition comprises BSO at a dosage of less than or equal to 50 mg/kg, or any other dosage described above, and the metallodrug is present at a clinically-acceptable dosage, as described above. For example, in some embodiments, the composition may comprise no more than 9 mg/day, preferably 3-9 mg of a metallodrug, such as auranofin. Alternatively, the composition may comprise no more than 100 mg/m$^2$, preferably between 30-100 mg/m$^2$ of a metallodrug, such as cisplatin. The ratio of BSO to the metallodrug is as described above. For example, the ratio of BSO to metallodrug may be 1:0.25 to 1:25, when the metallodrug is at a clinically-acceptable dosage. In some embodiments, the metallodrug is auranofin and the ratio of BSO to auranofin is 1:0.25 to 1:10. In other embodiments, the metallodrug is cisplatin and the ratio of BSO to metallodrug is 1:13 to 1:25.

The composition can comprise more than one metallodrug, and the more than one metallodrug can be as described above. The amounts and ratios of BSO and the more than one metallodrug are also as described above.

The composition is for the treatment of diseases as disclosed above. Cancer, rheumatic diseases and HIV are particularly preferred indications, and any of the diseases described above can be treated with the compositions of the invention.

BSO and the metallodrug can be administered using any suitable delivery technique known to those skilled in the art. For example, among other techniques, BSO and the metallodrug can be administered to a patient orally, by intravenous infusion or by injection, such as intramuscular injection.

In embodiments where BSO and a metallodrug are provided in a single composition, the composition is preferably administered by intramuscular injection.

EXAMPLES

Example 1

In-Vitro Activity on Activated CD4$^+$ T-Cells and Leukemia/Lymphoma

Methods. Resting CD4$^+$ T-cells, cultured T-cell leukemic Jurkat cells and Sup-T1 cells were left untreated or incubated for 24-72 hours with various concentrations of auranofin and/or buthionine sulfoximine (BSO), or chloroquine (only CD4$^+$ T-cells) or cisplatin (only Jurkat and Sup-T1 cells) CD4$^+$ T-cells were then activated by adding phytohemagglutinin (2 μg/mL). Alternatively, CD4$^+$ T-cells were first activated with anti-CD3/anti-CD28 beads and, after 72 hours, were left untreated or were incubated with auranofin and/or buthionine sulfoximine (BSO), or chloroquine. Cell viability was determined 24-72 hours post-activation with an MTT assay (CellTiter 96® Non-Radioactive Cell Proliferation Assay) or MTS assay (CellTiter 96® AQueous One Solution Cell Proliferation Assay System; Promega). For the assay, 300×10$^5$ cells were re-suspended in 100 μL of medium and transferred to a 96-well plate. Cells were then incubated with 20 μL of a substrate solution (One Solution Reagent) for 3-4 hours in a CO$_2$ (5%) incubator at 37° C. For the MTT assay, 100 μL of a Solubilization/Stop Solution were used to stop the reaction. Medium-only containing wells were included to serve as a blank control. Absorbance levels were recorded at 490 nm (MTS) or 570 nm (MTT) and, after subtraction of the blank, absorbance values were expressed as percentage of controls.

Results. The results from the new dosage combinations were compared to the untreated cells as well as the cells treated with single drugs or "classical" dosages, in a multiple comparison analysis. Thus, the statistical significances shown are also significant compared to the untreated cells.

Figure 1:
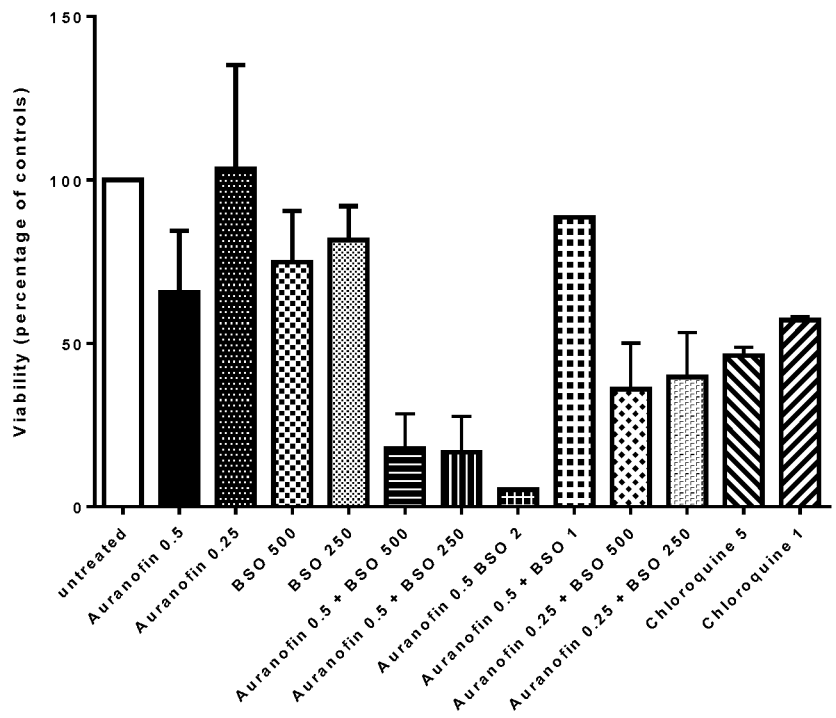
FIG. 1 is a graph showing the viability of activated primary CD4$^+$ T-cells treated with different concentrations of auranofin and buthionine sulfoximine (BSO), measured with the MTT assay. The cells were pre-incubated with the drugs for 24 hours and then activated with phytohemagglutinin (PHA) and assayed for viability 72 hours post activation (A) or the cells were activated with αCD3-αCD28 beads and then treated for 48 h with different combinations of auranofin and BSO (B). In (A), the effects of chloroquine are shown as a matter of comparison with a drug adopted in the clinic to limit immune hyperactivation. All concentrations are expressed in μM.
Figure 1:
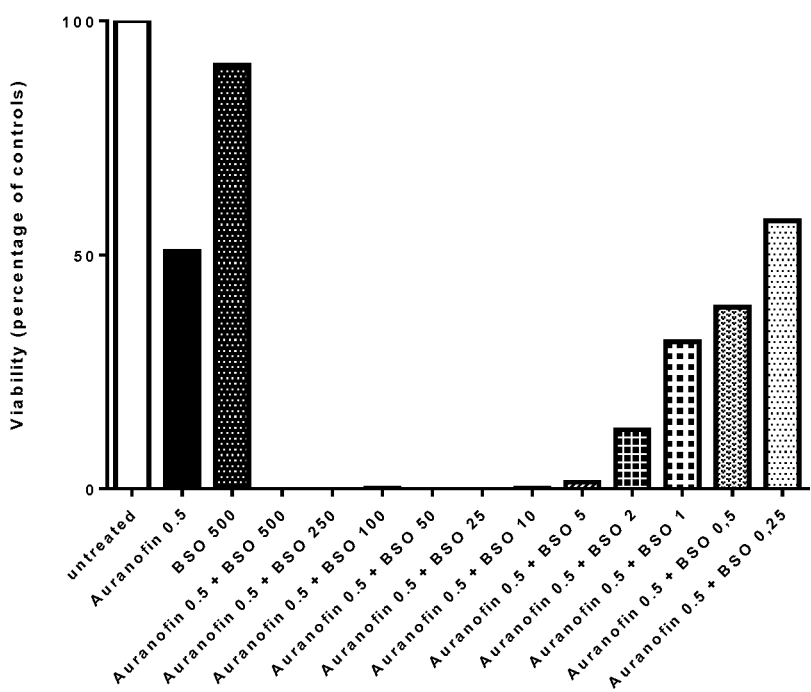

The results in FIG. 1 clearly show that concentrations as low as 2 μM of BSO have a synergistic effect with auranofin in limiting the viability of activated CD4$^+$ T-cells in a manner similar to a classically-described concentration (250 μM), and with an effect superior to that observed using clinically achievable concentrations of Chloroquine. Chloroquine is an immune-modulating drug being investigated against malignant immune hyperactivation in HIV/AIDS (Savarino and Shytaj, 2015). These effects were visible both when cells were pre-incubated with the drug combination (FIG. 1A) and when they were treated concomitantly to activation (FIG. 1B). FIG. 1B shows that the effects of BSO are still present when the drug is used at submicromolar concentrations.

Figure 2:
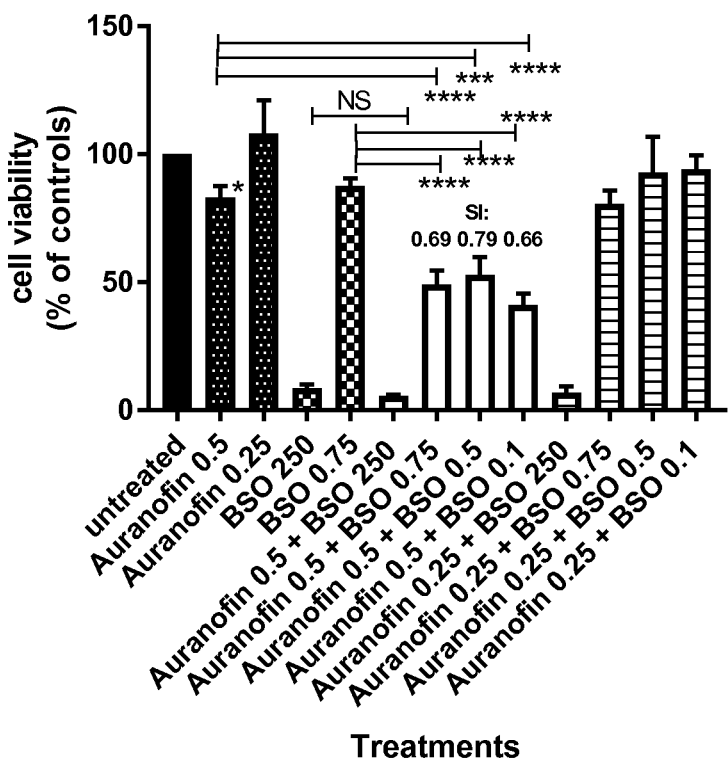
FIG. 2 is a graph showing the viability of Supt-1 T-cells treated with different concentrations of auranofin (AU) or buthionine sulfoximine (BSO). Viability was measured 72 hours after treatment with the drugs at the indicated concentrations with the MTS assay. Absorbance values were normalized over untreated controls and expressed as percentage. BSO=buthionine sulfoximine. Concentrations are expressed in μM. Data are expressed as mean±SEM and were analysed by the Turkey posttest following One Way ANOVA. *P<0.05; P<0.01 *P<0.001; ****P<0.0001. NS: non-significant. The synergistic index (SI) is expressed where significant differences exist in comparison with the single drug treatments.
Figure 3:
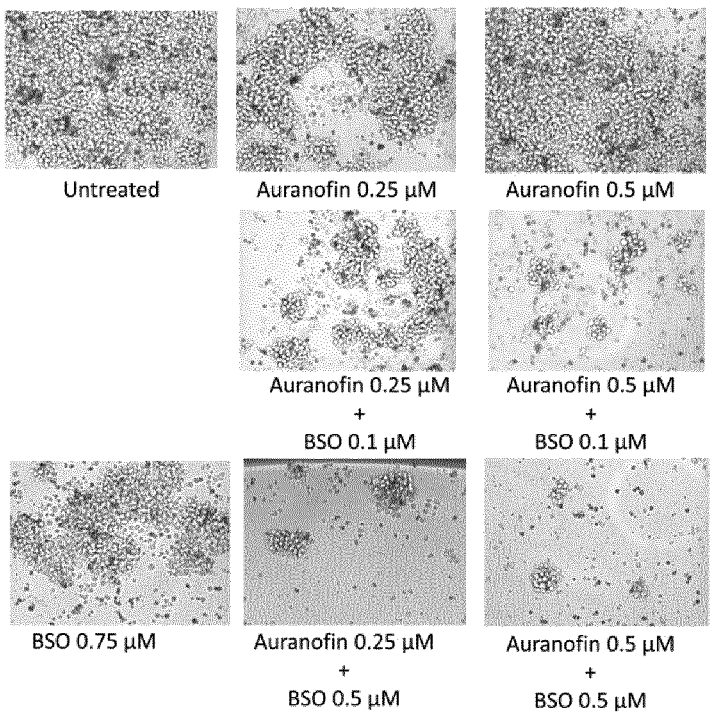
FIG. 3 is microphotographs of Supt-1 T-cells treated with different concentrations of auranofin or buthionine sulfoximine.

The results displayed in FIGS. 2 and 3 show that submicromolar concentrations of BSO induced a direct anticancer effect in the lymphoblastic Supt-1 cell line when used in combination with clinically-achievable auranofin concentrations. Surprisingly, a synergism with auranofin (synergistic index<0.9) was apparent only using the submicromolar range of BSO concentrations. In particular, although auranofin and BSO at a "classic" concentration of 250 μM showed low viability, the effects of the drug combination were not clear because the cytotoxic effect seen were ascribable to the effects of 250 μM of BSO only. Indeed, there was no significant difference between 250 μM of BSO only and the same BSO concentration in the presence of auranofin. Instead, using submicromolar BSO concentrations, there was an extremely significant difference between the effects of the combined drug treatments and the corresponding concentrations of the single drugs alone, yielding a synergistic index<0.9 (see, for example, BSO 0.75 alone and auranofin 0.5 alone, compared to auranofin 0.5+BSO 0.75).

Although FIG. 2 shows a significant synergism in terms of cell viability only with 0.5 μM of auranofin, FIG. 3 shows that 0.25 μM of auranofin in combination with submicromolar concentrations of BSO induces morphological alterations linked to poor lymphoblastic cell viability, such as disruption of clustering.

Significant synergism was also found with the combination of BSO and cisplatin, a metallodrug used in several chemotherapeutic protocols for leukemia/lymphoma treatment, in Jurkat T cells (a leukemic cell line; FIG. 4). In addition, the combination of auranofin and low concentrations of BSO was able to increase the anti-neoplastic effect of cisplatin (FIGS. 4 and 5). The effects observed in terms of cell viability were ascribable to the chemosensitizing effect of BSO on susceptibility to cisplatin (FIG. 4), and microscopic analysis of the treated cells showed that further addition of auranofin at a clinically-acceptable concentration increased the aforementioned morphological alterations linked to lymphoblastic cell death (FIG. 5).

Figure 6:
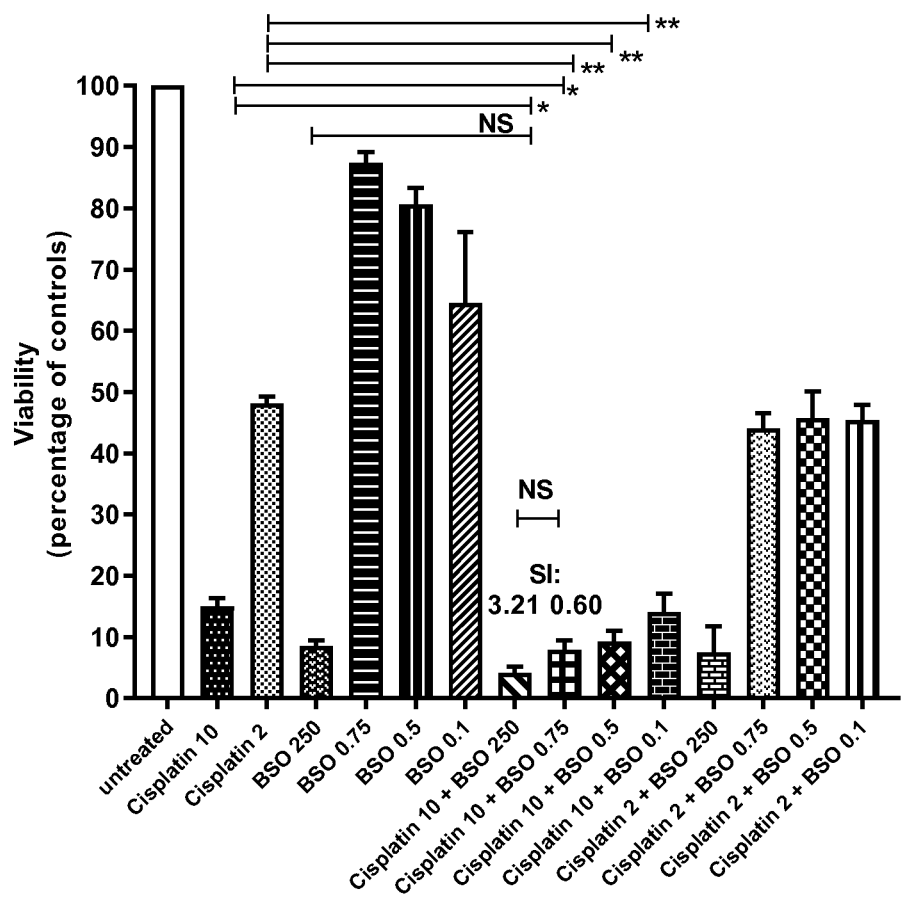
FIG. 6 is a graph showing the viability of Supt-1 T-cells treated with different concentrations of cisplatin or buthionine sulfoximine (BSO). Viability was measured 72 hours after treatment with the drugs at the indicated concentrations with the MTS assay. Absorbance values were normalized over untreated controls and expressed as percentage. BSO=buthionine sulfoximine. Concentrations are expressed in μM; Asterisks show the significant differences [*q<0.05; **q<0.01; q is the P value corrected for multiple comparisons by controlling the False Discovery Rate (threshold for significance=q=0.05)]. NS: non-significant. The synergistic index (SI) is expressed where significant differences exist in comparison with the single drug treatments.

A chemosentitizing effect of BSO on susceptibility to cisplatin was also detected in the Supt-1 cell line (FIG. 6). Surprisingly, in both cell lines, the submicromolar concentrations of BSO in combination with a clinically-acceptable concentration of cisplatin (10 µM) induced an inhibition of cellular proliferation similar to that obtained with a "classic" supramicromolar BSO concentration (250 µM; no statistical difference between treatments). Although 250 µM of BSO increased cisplatin-induced cell death, the effect was antagonistic (synergistic index>1.1; FIG. 6). Instead, a true synergism was observed by combining BSO at submicromolar concentrations and cisplatin at an average plasma concentration of 10 µM (FIGS. 4-6).

Example 2

Clinical Use

The following is a theoretical example for a typical situation wherein the BSO is used at a reduced concentration, with a clinically-acceptable dosage of auranofin to treat a patient with an HIV diagnosis.

Patient XX (male, 28 y.o.) received an HIV diagnosis in 2008. His viral load and CD4$^+$ T-cell counts resulted to be 48,000 plasma viral RNA copies/mL and 430 cells/µL, respectively. A standard therapy consisting of tenofovir/emtricitabine and efavirenz is started. Three months later, the CD4$^+$ T-cell count has risen to 680 cells/µL and viral load has dropped to undetectable levels. The situation is maintained essentially stable during the following nine years, and the only significant events is a switch from efavirenz to raltegravir and occasional viral blips with viral loads never rising above 500 viral RNA copies/mL.

The patient is subjected to quantification of viral DNA, the result of which is 22 copies/$10^6$ CD4$^+$ T-cells. The patient now starts a drug regimen comprising auranofin (6 mg bid for six months) and low-dose BSO (three one-week cycles at 0.08 g orally every 6 hours, intertwined by 3 weeks off BSO starting at month 3 of auranofin treatment). Background antiretroviral therapy is maintained during the entire six-month period. The computational simulations presented in Example 3 show that patient XX's viral reservoir decreases below the limit of detection of the most sensitive techniques, i.e. 10 copies of viral DNA/million cells, thus rendering him eligible for a structured treatment interruption aimed at exploring whether he will be able to maintain viral load under check spontaneously without any further therapeutic interventions.

Example 3

Computational Simulations.

Computational simulations of the latently HIV-infected cell dynamics were based on the system of differential equations developed by Rong and Perelson (Rong and Perelson; 2009), applying the baseline parameters as shown by the same authors. Numerical simulations were performed with the ordinary differential equations solver of the Mathlab software. The proliferation-upon-activation rate (henceforth, proliferation rate) was decreased from 1.4 day$^{-1}$ (normal rate) to 0.56, 0.28 and 0.14 day$^{-1}$.

Figure 7:
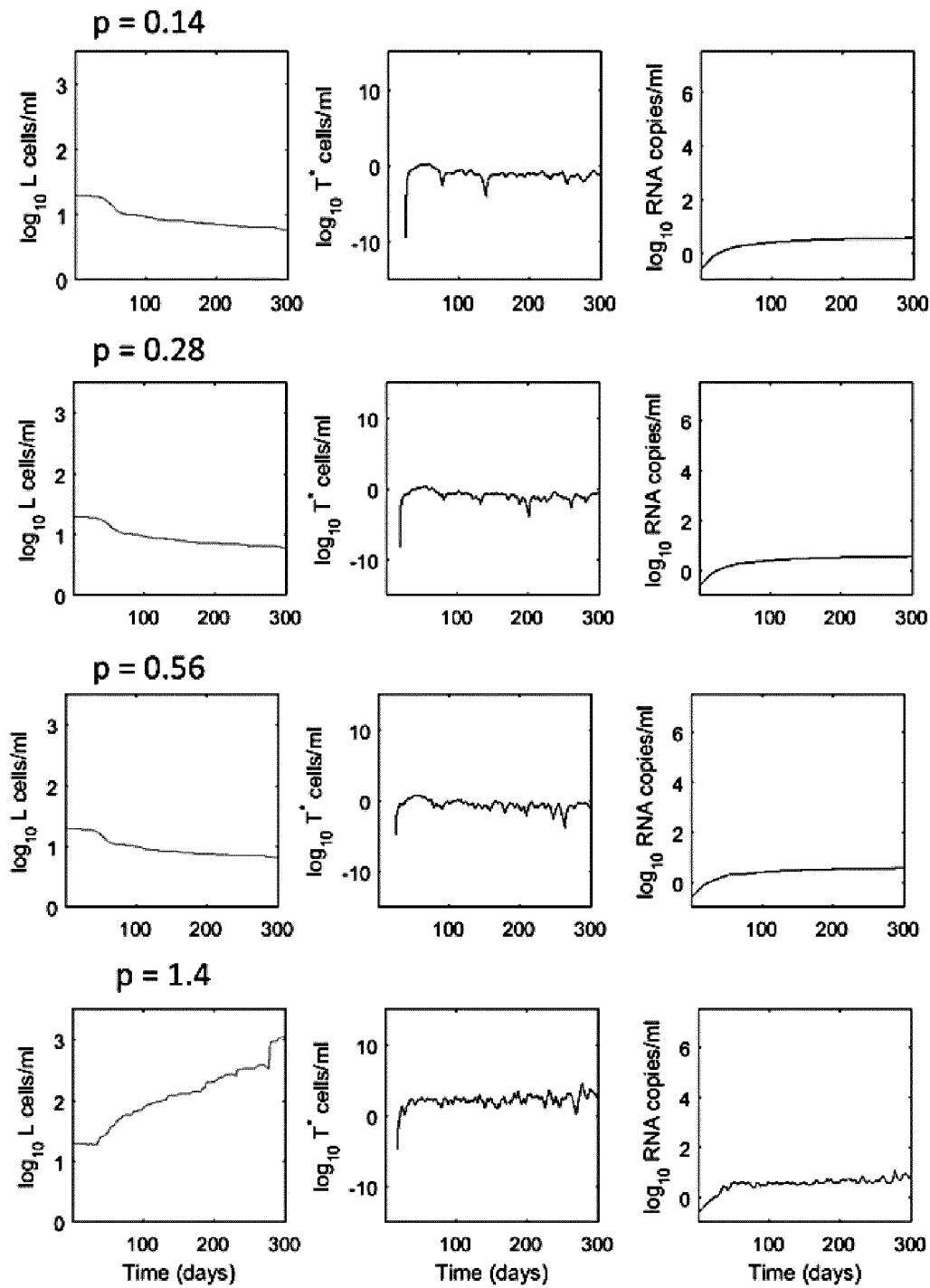
FIG. 7 shows the results of numerical simulations of the Rong and Perelson model with programmed expansion and contraction of the viral reservoir. A simulation of the viral load (RNA copies/nil) and viral reservoir (L cells) dynamics in a human model is provided. The trend of productively infected cells (T*) is also shown. The simulation is based on the five differential equations model in Rong and Perelson (2009). The peaks in the viral load correspond to the periods of activation of latently infected CD4+ T-cells. For starting data see Rong and Perelson (2009). Different proliferation rates (p) are shown (day$^{-1}$), corresponding to different drug treatments, or absence of any treatment. The bottom three panels depict a scenario without the drugs, with p=1.4 day$^{-1}$. The effects of BSO in combination with auranofin at plasma molar ratios (BSO/auranofin) of 1:0.25 (top three panels), 1:0.5 (second line of panels from top), 1:1 (third line of panels from top) are simulated. The plasma concentration of auranofin is 500 microM. The activation function adopted to simulate lymphocyte encounter with antigens is illustrated in Rong and Perelson (2009).

The results showed that the viral reservoir decayed when the lymphocyte proliferation rate was decreased, but, unexpectedly, its decay rate was partially independent of the size of the decrease of the proliferation rate (FIG. 7). These results further support a scenario wherein low BSO dosages may be added to clinically-achievable auranofin dosages, and suggest a possibility of therapeutic success also in case this pharmacological combination should not reach the same level of in vivo anti-lymphoproliferative efficacy caused by the "classical" auranofin/BSO combinations containing higher amounts of BSO.

REFERENCES

Anderson C P, Matthay K K, Perentesis J P, Neglia J P, Bailey H H, Villablanca J G, Groshen S, Hasenauer B, Maris J M, Seeger R C, Reynolds C P; "Pilot study of intravenous melphalan combined with continuous infusion L-S,R-buthionine sulfoximine for children with recurrent neuroblastoma". Pediatr Blood Cancer. 2015 October; 62(10):1739-46. doi: 10.1002/pbc.25594.

Bailey H H, Mulcahy R T, Tutsch K D, Arzoomanian R Z, Alberti D, Tombes M B, Wilding G, Pomplun M, Spriggs D R; "Phase I clinical trial of intravenous L-buthionine sulfoximine and melphalan: an attempt at modulation of glutathione". J Clin Oncol. 1994 January; 12(1):194-205.

Bailey H H, Ripple G, Tutsch K D, Arzoomanian R Z, Alberti D, Feierabend C, Mahvi D, Schink J, Pomplun M, Mulcahy R T, Wilding G; "Phase I study of continuous-infusion L-S,R-buthionine sulfoximine with intravenous melphalan. J Natl Cancer Inst. 1997 Dec. 3; 89(23):1789-96.

Benhar M, Shytaj I L, Stamler J S, Savarino A; "Dual targeting of the thioredoxin and glutathione systems in cancer and HIV". J Clin Invest. 2016 May 2; 126(5): 1630-9. doi: 10.1172/JCI85339. Review.

Capparelli E V, Bricker-Ford R, Rogers M J, McKerrow J H, Reed S L, "Phase I Clinical Trial Results of Auranofin, a Novel Antiparasitic Agent", Antimicrob Agents Chemother, vol. 61(1), January 2017, e01947-16.

Griffith O W, Meister A; "Potent and specific inhibition of glutathione synthesis by buthionine sulfoximine (S-n-butyl homocysteine sulfoximine)". J Biol Chem. 1979 Aug. 25; 254(16):7558-60.

Malaker K, Hurwitz S J, Bump E A, Griffith O W, Lai L L, Riese N, Coleman C N; "Pharmacodynamics of prolonged treatment with L,S-buthionine sulfoximine". Int J Radiat Oncol Biol Phys. 1994 May 15; 29(2):407-12.

Mayer R D, Lee K E, Cockett A T. Improved use of buthionine sulfoximine to prevent cisplatin nephrotoxicity in rats. J Cancer Res Clin Oncol. 1989; 115(5):418-22. PubMed PMID: 2808478.

Meister A; "Glutathione deficiency produced by inhibition of its synthesis, and its reversal; applications in research and therapy". Pharmacol Ther. 1991; 51(2):155-94. Review.

O'Dwyer P J, Hamilton T C, Young R C, LaCreta F P, Carp N, Tew K D, Padavic K, Comis R L, Ozols R F. "Depletion of glutathione in normal and malignant human cells in vivo by buthionine sulfoximine: clinical and biochemical results", J Natl Cancer Inst. 1992 Feb. 19; 84(4):264-7.

O'Dwyer P J, Hamilton T C, LaCreta F P, Gallo J M, Kilpatrick D, Halbherr T, Brennan J, Bookman M A, Hoffman J, Young R C, Comis R L, Ozols R F; "Phase I trial of buthionine sulfoximine in combination with melphalan in patients with cancer". J Clin Oncol. 1996 January; 14(1):249-56.

Rong L, Perelson A S; "Modeling latently infected cell activation: viral and latent reservoir persistence, and viral blips in HIV-infected patients on potent therapy". PLoS Comput Biol. 2009 October; 5(10):e1000533. doi: 10.1371/journal.pcbi.1000533.

Sandor V, Flarakos T, Batist G, Wainer I W, Lloyd D K, "Quantitation of the diastereoisomers of l-buthionine-(R, S)-sulfoximine in human plasma: a validated assay by capillary electrophoresis", J Chromatogr B Biomed Sci Appl, vol. 673 (1), 3 November 1995, p. 123-131.

Savarino A, Shytaj I L; "Chloroquine and beyond: exploring anti-rheumatic drugs to reduce immune hyperactivation in HIV/AIDS". Retrovirology. 2015 Jun. 18; 12:51. doi: 10.1186/s12977-015-0178-0. Review.

Shytaj I L, Chirullo B, Wagner W, Ferrari M G, Sgarbanti R, Corte A D, LaBranche C, Lopalco L, Palamara A T, Montefiori D, Lewis M G, Garaci E, Savarino A; "Investigational treatment suspension and enhanced cell-mediated immunity at rebound followed by drug-free remission of simian AIDS". Retrovirology. 2013 Jul. 16; 10:71. doi: 10.1186/1742-4690-10-71.

Shytaj I L, Nickel G, Arts E, Farrell N, Biffoni M, Pal R, Chung H K, LaBranche C, Montefiori D, Vargas-Inchaustegui D, Robert-Guroff M, Lewis M G, Sacha J B, Palamara A T, Savarino A; "Two-Year Follow-Up of Macaques Developing Intermittent Control of the Human Immunodeficiency Virus Homolog Simian Immunodeficiency Virus SIVmac251 in the Chronic Phase of Infection". J Virol. 2015 August; 89(15):7521-35.doi: 10.1128/JVI.00396-15.

Suarez-Almazor M E, Spooner C H, Belseck E, Shea B; "Auranofin versus placebo in rheumatoid arthritis". Cochrane Database Syst Rev. 2000; (2):CD002048. Review.

Tsutsui K, Komuro C, Ono K, Nishidai T, Shibamoto Y, Takahashi M, Abe M. "Chemosensitization by buthionine sulfoximine in vivo", Int J Radiat Oncol Biol Phys, 1986 Jull 12(7): 1183-6

Villablanca et al., "A Phase I New Approaches to Neuroblastoma Therapy Study of Buthionine Sulfoximine and Melphalan With Autologous Stem Cells for Recurrent/Refractory High-Risk Neuroblastoma", Pediatr Blood Cancer. 2016 August; 63(8):1349-56.

Vint I A, Chain B M, Foreman J C; "The interaction of auranofin and buthionine sulfoximine blocks activation of human peripheral T lymphocytes". Cell Immunol. 1993 November; 152(1):152-61.

Wang H, Bouzakoura S, Mey S, Jiang H, Law K, Dufait I, Corbet C, Verovski V, Gevaert T, Feron O, Van den Berge D, Storme G, De Ridder M; "Auranofin radiosensitizes tumor cells through targeting thioredoxin reductase and resulting overproduction of reactive oxygen species". Oncotarget 2017 March, 5. doi: 10.18632/oncotarget.16113

You, B R, Shin H R, Han B, Kim S H, Park W H; "Auranofin induces apoptosis and necrosis in HeLa cells via oxidative stress and glutathione depletion". Molecular medicine reports 112 (2015): 1428-34.

The invention claimed is:

1. A method of treating malignant immune hyperactivation in a human, wherein the method comprises administering:
   (a) buthionine sulfoximine (BSO) at a dosage of less than or equal to 9 mg/kg, and
   (b) a gold-containing metallodrug at a clinically-acceptable dosage.

2. A method according to claim 1, wherein the malignant immune hyperactivation is cancer, HIV or a rheumatic disease.

3. A method according to claim 2, wherein the cancer is haematological malignancy, Hodgkin's lymphoma, non-Hodgkin's lymphoma, lung carcinoma, prostate cancer, hepatocellular carcinoma, breast cancer, glioblastoma, uterine cervix carcinoma or Kaposi's sarcoma.

4. A method according to claim 1, wherein the BSO is administered at a dosage of between 0.45 mg/kg and 9 mg/kg.

5. A method according to claim 1, wherein the malignant immune hyperactivation is HIV or a rheumatic disease.

6. A method according to claim 1, wherein the malignant immune hyperactivation is rheumatic arthritis or lupus.

7. A method according to claim 1, wherein the gold-containing metallodrug comprises auranofin, aurothioglucose and/or aurothiomalate.

8. A method according to claim 1, wherein the in vivo molar ratio of BSO to gold-containing metallodrug is 1:0.25 to 1:10.

9. A method according to claim 8, wherein the malignant immune hyperactivation is cancer and the in vivo molar ratio of BSO to gold-containing metallodrug is 1:0.5 to 1:10.

10. A method according to claim 8, wherein the malignant immune hyperactivation is HIV or a rheumatic disease, and the in vivo molar ratio of BSO to gold-containing metallodrug is 1:0.25 to 1:1.

11. A method according to claim 1, wherein the gold-containing metallodrug comprises auranofin administered at a dosage of 3-9 mg/day.

12. A method according to claim 1, wherein the malignant immune hyperactivation is HIV or a rheumatic disease, and wherein the method comprises administering to a patient in need thereof:
   (a) BSO at a dosage sufficient to achieve a peak plasma concentration of 0.5-20 µM, and
   (b) a gold-containing metallodrug at a clinically-acceptable dosage.

13. A method according to claim 1, wherein the malignant immune hyperactivation is cancer, and wherein the method comprises administering to a patient in need thereof:
   (a) BSO at a dosage sufficient to achieve a mean plasma concentration of 0.05-0.8 µM, and
   (b) a gold-containing metallodrug at a clinically-acceptable dosage.

14. A kit comprising BSO and a gold-containing metallodrug, wherein:
   (a) the BSO is at a dosage of less than or equal to 900 mg, and
   (b) the gold-containing metallodrug is at a clinically-acceptable dosage.

15. A pharmaceutical composition comprising BSO and a gold-containing metallodrug, wherein the gold-containing metallodrug is present at a clinically-acceptable amount for administration to humans and the molar ratio of BSO to the gold-containing metallodrug is 1:0.003 or lower, and wherein the pharmaceutical composition comprises a pharmaceutically-acceptable carrier, diluent and/or excipient.

* * * * *